(12) United States Patent
Jeffress

(10) Patent No.: US 7,847,947 B2
(45) Date of Patent: Dec. 7, 2010

(54) SPECTROSCOPIC LANCE FOR BULK SAMPLING

(76) Inventor: Colin Jeffress, 29 Churchill Road North, South Australia (AU) 5094

( * ) Notice: Subject to any disclaimer, the term of this patent is extended or adjusted under 35 U.S.C. 154(b) by 312 days.

(21) Appl. No.: 11/917,019

(22) PCT Filed: Jun. 27, 2006

(86) PCT No.: PCT/AU2006/000897
§ 371 (c)(1), (2), (4) Date: Dec. 10, 2007

(87) PCT Pub. No.: WO2007/000018
PCT Pub. Date: Jan. 4, 2007

(65) Prior Publication Data
US 2008/0212077 A1    Sep. 4, 2008

(30) Foreign Application Priority Data
Jun. 27, 2005    (AU) ............................... 2005903371

(51) Int. Cl.
*G01N 21/00* (2006.01)
*G01N 21/55* (2006.01)
(52) U.S. Cl. .................... 356/445; 356/241.1
(58) Field of Classification Search ................ 356/445, 356/241.1–241.6, 614, 625, 300; 250/559.07, 250/559.22, 559.39, 559.49; 73/865.5, 865.8
See application file for complete search history.

(56) References Cited

U.S. PATENT DOCUMENTS

| | | | | |
|---|---|---|---|---|
| 4,355,904 A | * | 10/1982 | Balasubramanian | ........ 356/608 |
| 4,829,186 A | | 5/1989 | McLachlan et al. | |
| 4,900,933 A | * | 2/1990 | Nestor et al. | ............. 250/458.1 |
| 4,967,092 A | * | 10/1990 | Fraignier et al. | ........ 250/559.07 |
| 5,051,551 A | | 9/1991 | Dowyle | |
| 5,177,779 A | * | 1/1993 | Cornu et al. | ................ 378/206 |
| 5,351,322 A | | 9/1994 | Vonbargen | |
| 5,416,574 A | * | 5/1995 | Fantone | ..................... 356/124 |
| 5,459,316 A | | 10/1995 | Doyle | |
| 5,621,522 A | | 4/1997 | Ewing et al. | |
| 5,822,072 A | | 10/1998 | Dai et al. | |
| 5,933,231 A | * | 8/1999 | Bieman et al. | ........... 356/241.1 |
| 5,946,089 A | * | 8/1999 | Duer | ......................... 356/318 |
| 6,535,283 B1 | * | 3/2003 | Heffels et al. | ............... 356/300 |

(Continued)

FOREIGN PATENT DOCUMENTS

DE    102004020350 A1    11/2005

(Continued)

*Primary Examiner*—Sang Nguyen
(74) *Attorney, Agent, or Firm*—David A. Guerra

(57) ABSTRACT

A lance assembly (10) for spectroscopically sampling bulk product (8) is disclosed. The assembly comprises: an elongate lance body (11) having a longitudinal axis (15), a proximal end (12) for maneuvering and a head (19) defining a cavity (18). Housed within the cavity (18) is a spectroscopic receiver (20) having a field of view and a radiant energy source (40) providing a beam of energy to be reflected from the bulk product (8) to the receiver 20 through a window (30). The window (30) has an external surface (31) which, in use, is in contact with the bulk product (8). The beam of energy and the field of view of the receiver (20) are both directed towards the external surface (31) so as to allow sampling adjacent the external surface (31).

16 Claims, 6 Drawing Sheets

U.S. PATENT DOCUMENTS

| | | |
|---|---|---|
| 6,762,827 B2 * | 7/2004 | Aroussi et al. .................. 356/28 |
| 7,164,476 B2 * | 1/2007 | Shima et al. .............. 356/241.1 |
| 7,245,373 B2 * | 7/2007 | Soller et al. ................... 356/325 |
| 7,382,458 B2 * | 6/2008 | Johnson et al. .............. 356/436 |
| 7,535,564 B2 * | 5/2009 | Di Fabrizio et al. ....... 356/241.1 |
| 7,557,914 B2 * | 7/2009 | Thompson et al. ........ 356/241.1 |
| 2002/0126289 A1 | 9/2002 | Marquardt et al. |
| 2003/0197125 A1 | 10/2003 | De Saro et al. |

FOREIGN PATENT DOCUMENTS

| | | |
|---|---|---|
| WO | 01/69213 A2 | 9/2001 |
| WO | 02/077608 A2 | 10/2002 |

\* cited by examiner

SPECTROSCOPIC LANCE FOR BULK SAMPLING

CROSS-REFERENCE TO RELATED APPLICATIONS

This application is an U.S. national phase application under 35 U.S.C. §371 based upon co-pending International Application No. PCT/AU2006/000897 filed on Jun. 27, 2006. Additionally, this U.S. national phase application claims the benefit of priority of co-pending International Application No. PCT/AU2006/000897 filed on Jun. 27, 2005 and Australia Application No. 2005903371 filed on Jun. 27, 2005. The entire disclosures of the prior applications are incorporated herein by reference. The international application was published on Jan. 4, 2007 under Publication No. WO 2007/000018 A1.

FIELD OF THE INVENTION

The present invention relates to sampling of bulk product and in particular to methods and apparatus for spectroscopically analysing samples of bulk product.

BACKGROUND OF THE INVENTION

Analysis of samples of material by spectroscopic methods, eg near infrared spectroscopy, is a well documented procedure, using the spectroscopic signature of a material to determine its physical and chemical properties. This methodology is typically used to quantify the quality and characteristics of materials delivered to bulk receiving centres by taking a small sample of the material (which is supposed to statistically represent the whole mass) and subjecting the sample to laboratory spectroscopic analysis. Using well understood techniques and commercially available spectrometers and computer statistical software, database and chemometric calibrations are applied to determine the parameters of the sample. This methodology is applied in such industries as grain handling at silos, wine grape receiving at wineries and environmental disposal centres. Those delivering products may be paid for the quality/characteristics of the delivered material based on this analysis and the analysis may be used to group or store the received material.

The deficiencies in current systems are the difficulty in taking representative samples, the difficulty in removing and processing the samples, the laboratory handling of the samples and the time taken to produce a result. This is especially important when subsequent handling and movement of the delivered product is dependent on the result of the analysis, often causing a delay in production processes.

By way of example, when a grower delivers a truckload of wine grapes to a winery receiving centre, samples of the load are usually taken with a mechanical device which plunges into the load and removes a quantity of grapes from up to four different places by a complex mechanical shutter arrangement. The extracted sample is then disgorged, examined by hand and a subsample of grapes removed for "colour" analysis by near infrared spectroscopy in the laboratory. Then a juice sample (from the natural pressing of the weight of the grapes in the truck) is removed from the bottom layer of the truck by a suction process and the juice subjected to further laboratory handling to produce values for brix and other parameters by near infrared spectroscopy. The results of these processes are then used by the winemaker to determine grower payment and how the grape load will be handled for crushing (ie used for premium wine, specialty wine or for lower value bulk wine). These decisions must be made "on the fly" and the driver directed to the appropriate crushing unit with as little delay as possible.

Likewise, when a bulk load of grain is delivered to a silo, samples of the load are removed by a vacuum lance and the aggregate taken into the laboratory. A small subsample is then placed in a cuvette, petri dish or sample holder and placed into a spectrometer for analysis of parameters such as protein and moisture. The result of this analysis is used for grower payment, type determination, quality designation, holding location and subsequent storage.

These current methods are far slower than industry would like and there are questions over the statistical validity of the small samples actually tested.

It is an object of the invention to provide a method and apparatus for spectroscopically sampling bulk product that overcomes or ameliorates at least some of the aforementioned deficiencies and problems.

SUMMARY OF THE INVENTION

According to a first aspect of the invention there is provided a lance assembly for spectroscopically sampling bulk product, the assembly comprising:
 an elongate lance body having a longitudinal axis, a proximal end for maneuvering and a head defining a cavity;
 a spectroscopic receiver housed within the cavity, the receiver having a field of view;
 a radiant energy source providing a beam of energy to be reflected from the bulk product to the receiver; and
 a window on the head, the window allowing transmission of a reflected spectroscopic signal through the field of view to the receiver from a position adjacent the window, the window having an external surface, in use the external surface in contact with the bulk product,
 whereby the beam of energy and the field of view of the receiver are both directed towards the external surface so as to allow sampling adjacent the external surface.

Preferably the external surface includes a sampling area angled with respect to a plane normal to the longitudinal axis,
 whereby in use bulk product flows past the sampling area of the external surface as the head is advanced into the bulk product.

Preferably the external surface is planar and wherein the planar external surface is angled with respect to a plane normal to the longitudinal axis,
 whereby in use bulk product flows past the external surface as the head is advanced into the bulk product.

Preferably the planar external surface is angled between 45 and 90 degrees with respect to a plane normal to the longitudinal axis.

Preferably the assembly further comprises a spectrometer housed within the cavity, the spectrometer incorporating the receiver.

Preferably the head is removable to facilitate access to the cavity and the spectrometer.

Preferably both the beam of radiant energy and the field of view of the receiver are orientated at an angle of less than 90 degrees from the planar external surface,
 whereby direct reflections of the beam of light from surfaces parallel to the external surface are directed away from the field of view.

Preferably the assembly further comprises a camera for imaging analysis.

Preferably the camera is positioned angularly between the radiant energy source and the receiver.

Preferably the assembly further comprises a driving and positioning system for driving and positioning the head into the bulk product.

According to a second aspect of the invention there is provided a method for spectroscopically sampling bulk product comprising the steps of:

presenting the bulk product in a bulk vessel to an analysis station;

maneuvering an elongate lance assembly having a longitudinal axis and housing a radiant energy source and a spectroscopic receiver with respect to the bulk product so as to penetrate the bulk product within the vessel;

receiving a spectroscopic signal from a sample of the bulk product;

analysing the spectroscopic signal to provide information as to constituent parameters of the sample; and conveying information pertaining to the constituent parameters of the sample to an operator or to a data collection system.

According to a third aspect of the invention there is provided a method for spectroscopically sampling bulk product comprising the steps of:

transporting the bulk product in a vehicle to an analysis station;

maneuvering an elongate lance assembly having a longitudinal axis and housing a radiant energy source and a spectroscopic receiver with respect to the bulk product so as to penetrate the bulk product within the vehicle;

receiving a spectroscopic signal from a sample of the bulk product;

analysing the spectroscopic signal to provide information as to constituent parameters of the sample; and conveying information on the quality of the sample to an operator.

Specific embodiments of the invention will now be described in some further detail with reference to and as illustrated in the accompanying figures. These embodiments are illustrative, and are not meant to be restrictive of the scope of the invention.

DESCRIPTION OF THE DRAWINGS

In order that the present invention can be clearly understood and put into practical effect, the description will now refer to the drawings which show non-limiting embodiments of the invention.

DETAILED DESCRIPTION OF THE PREFERRED EMBODIMENTS OF THE INVENTION

Figure 1:
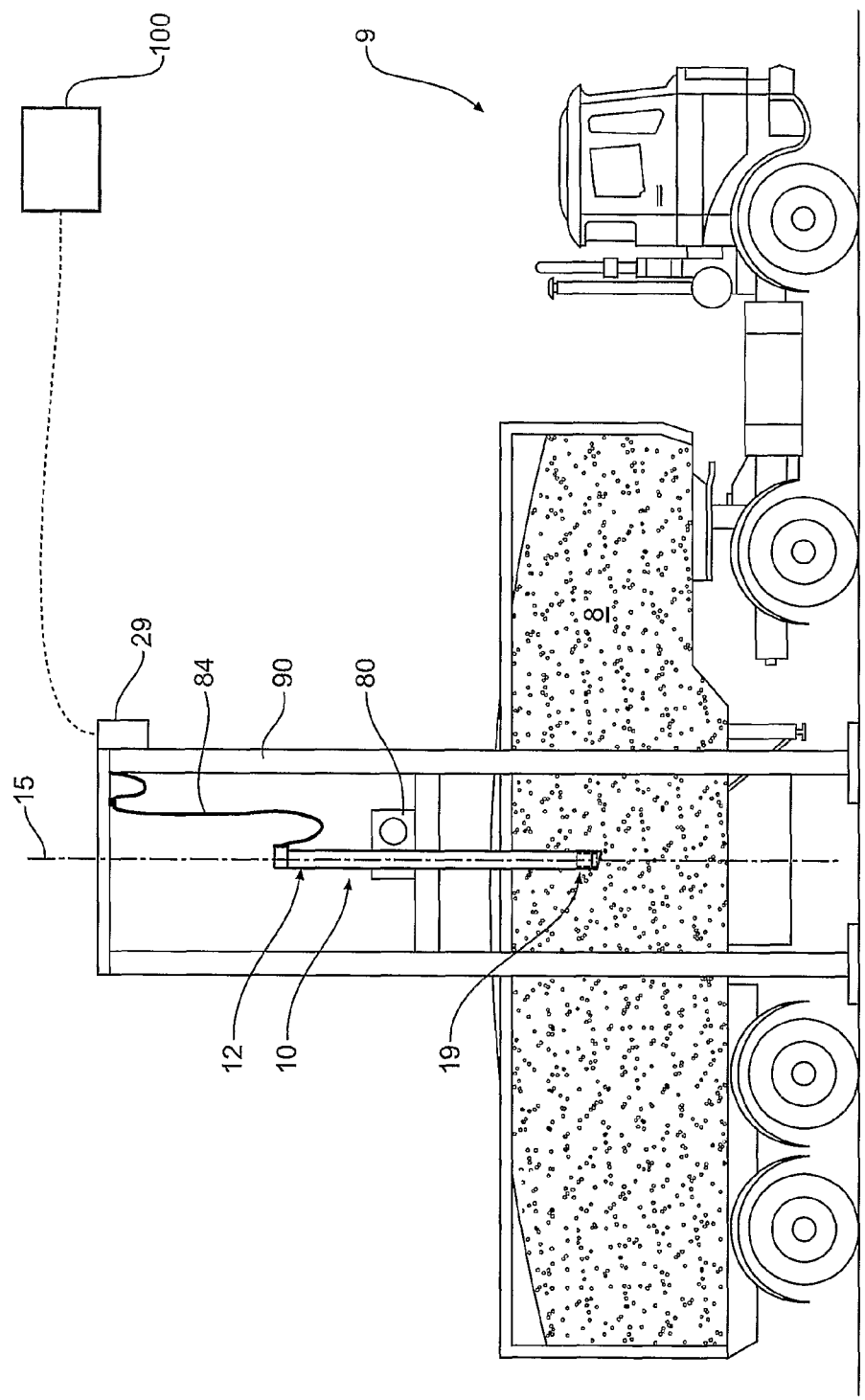
FIG. 1 is a schematic representation of a spectroscopic lance assembly for bulk sampling mounted with its positioning mechanism over a vehicle delivering bulk material.
Figure 2:
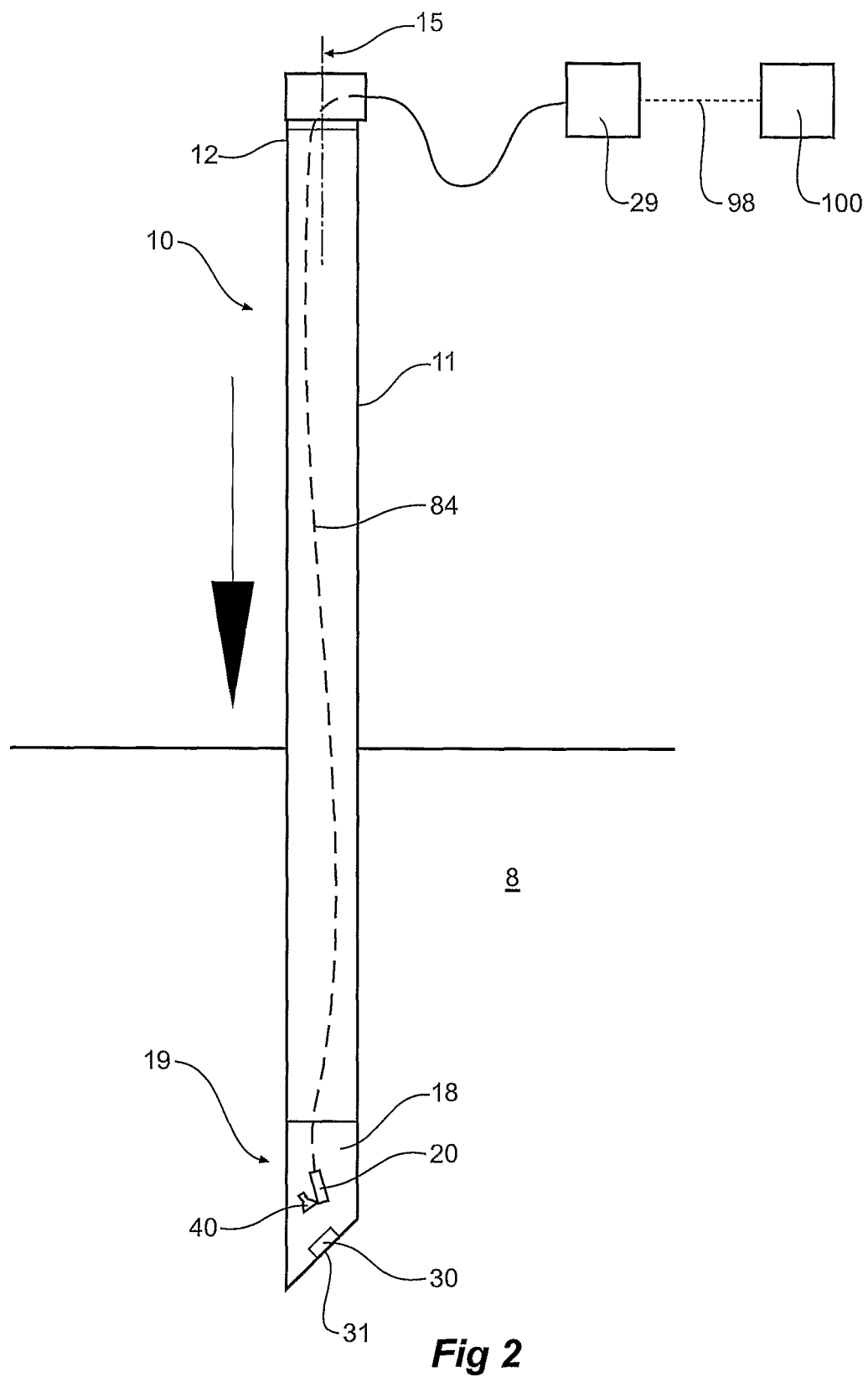
FIG. 2 is a schematic view of the lance assembly of FIG. 1.

Referring to FIGS. 1 and 2, a lance assembly 10 for spectroscopically sampling bulk product 8 is shown. The assembly 10 comprises an elongate lance body 11 having a longitudinal axis 15, a proximal end 12 for maneuvering and a head 19 defining a cavity 18. A spectroscopic receiver 20 is housed within the cavity 18. A radiant energy source (or light source) 40 is provided behind a window 30. In use, a beam of light from the light source passes through the window 30 and is reflected from bulk product 8 to the spectroscopic receiver 20 for analysis.

Referring again to FIG. 1, the lance assembly 10 is shown within a receiving station for wine grapes at a winery, where the quality and parameters of grapes are assessed as the truck 9 carrying the grapes from the grower arrive at a weigh bridge. This arrangement facilitates the calculation of payment to be made to the grape grower and facilitates direction of the truck 9 to an appropriate crusher for the most appropriate and economic use of the grapes. A similar system could be appropriate for receiving and classifying grain at a silo or bulk grain receiving centre.

Figure 3:
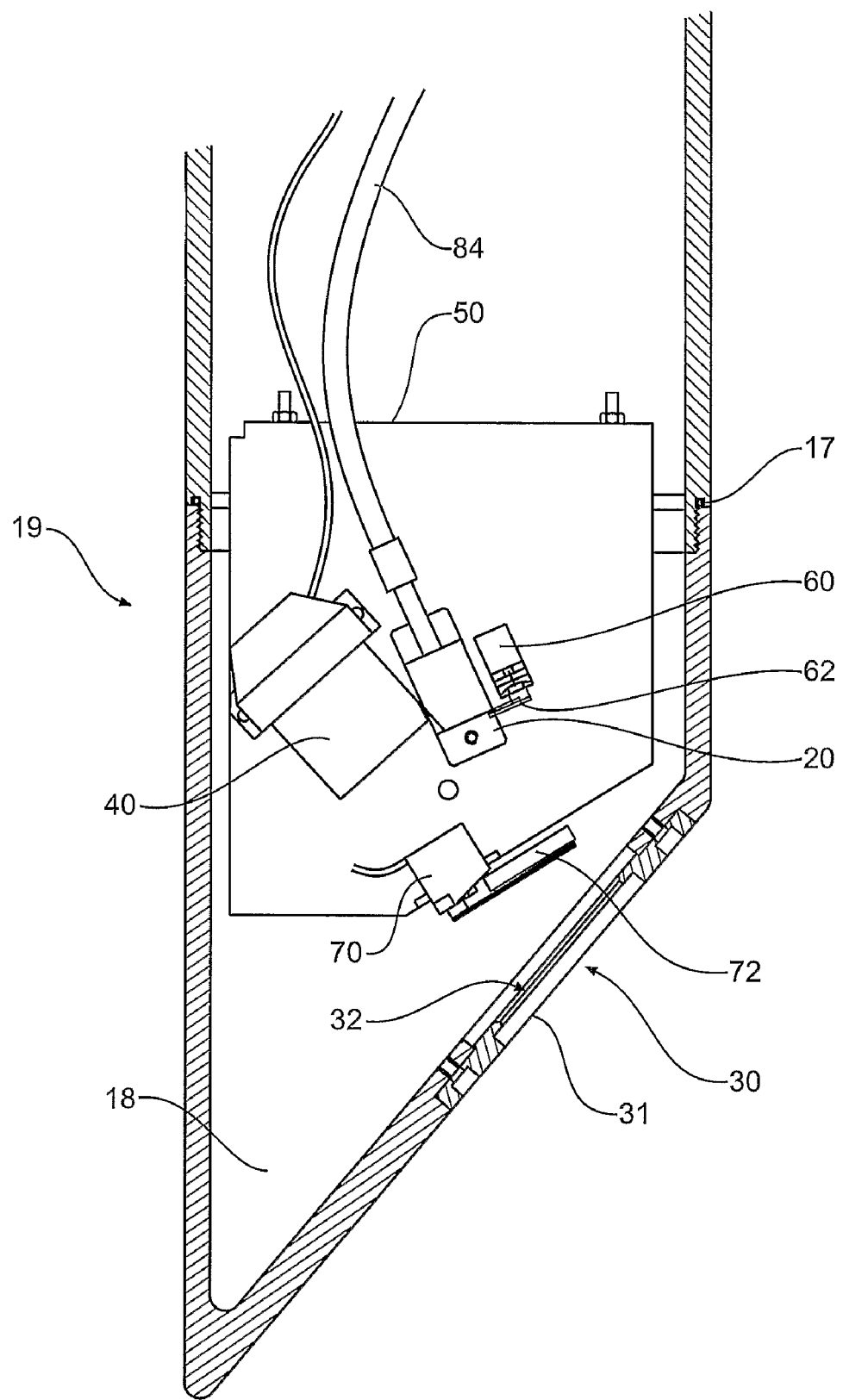
FIG. 3 is a cross sectional schematic view of the distal end of the lance assembly shown in FIG. 2.

The lance assembly 10 is shown in more detail in the cross sectional schematic view of FIG. 3. The light source 40 provides a beam of energy (or light) 42 that is shown illustratively between lines 46 and 48 on FIG. 6. The window 30 has an external surface 31 and an internal surface 32. In use, the external surface 31 is in direct contact with the bulk product 8 as is shown in FIG. 1. Sampling is possible at a location adjacently external surface 31 because the beam of light and the field of view of the receiver are both directed towards the external surface 31.

Figure 4:
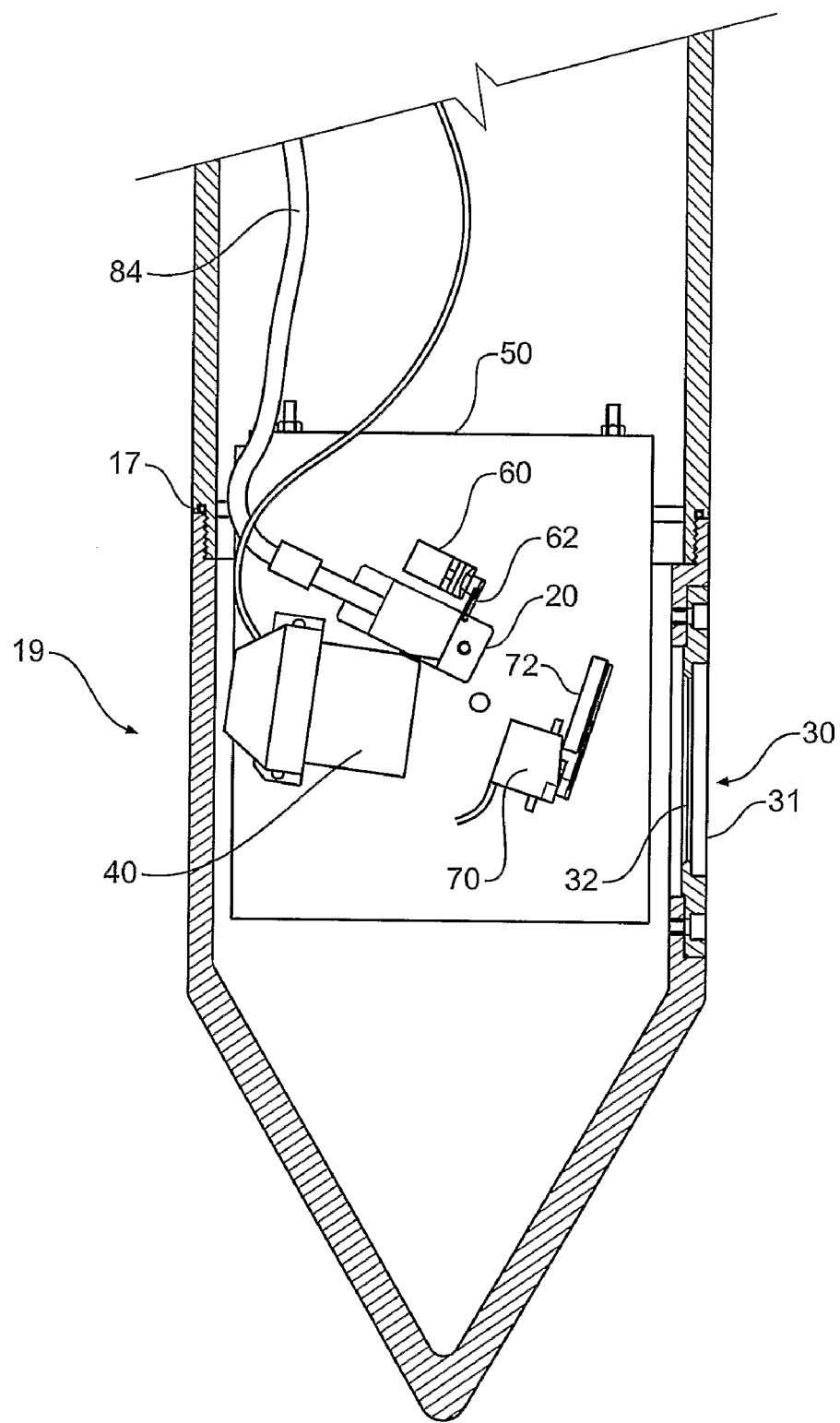
FIG. 4 is a similar view to that of FIG. 3 but shows an alternative embodiment.

The external surface 31 is planar and is angled with respect to a plane normal to the longitudinal axis 15. This angling of the external surface 31 allows bulk product 8 to flow past the external surface 31 as the head 19 is advanced into the bulk product 8. With the embodiment of the invention illustrated in FIG. 3, the angle is approximately 50°. In other applications, the angle could be 90 degrees as is shown in FIG. 4.

Figure 5:
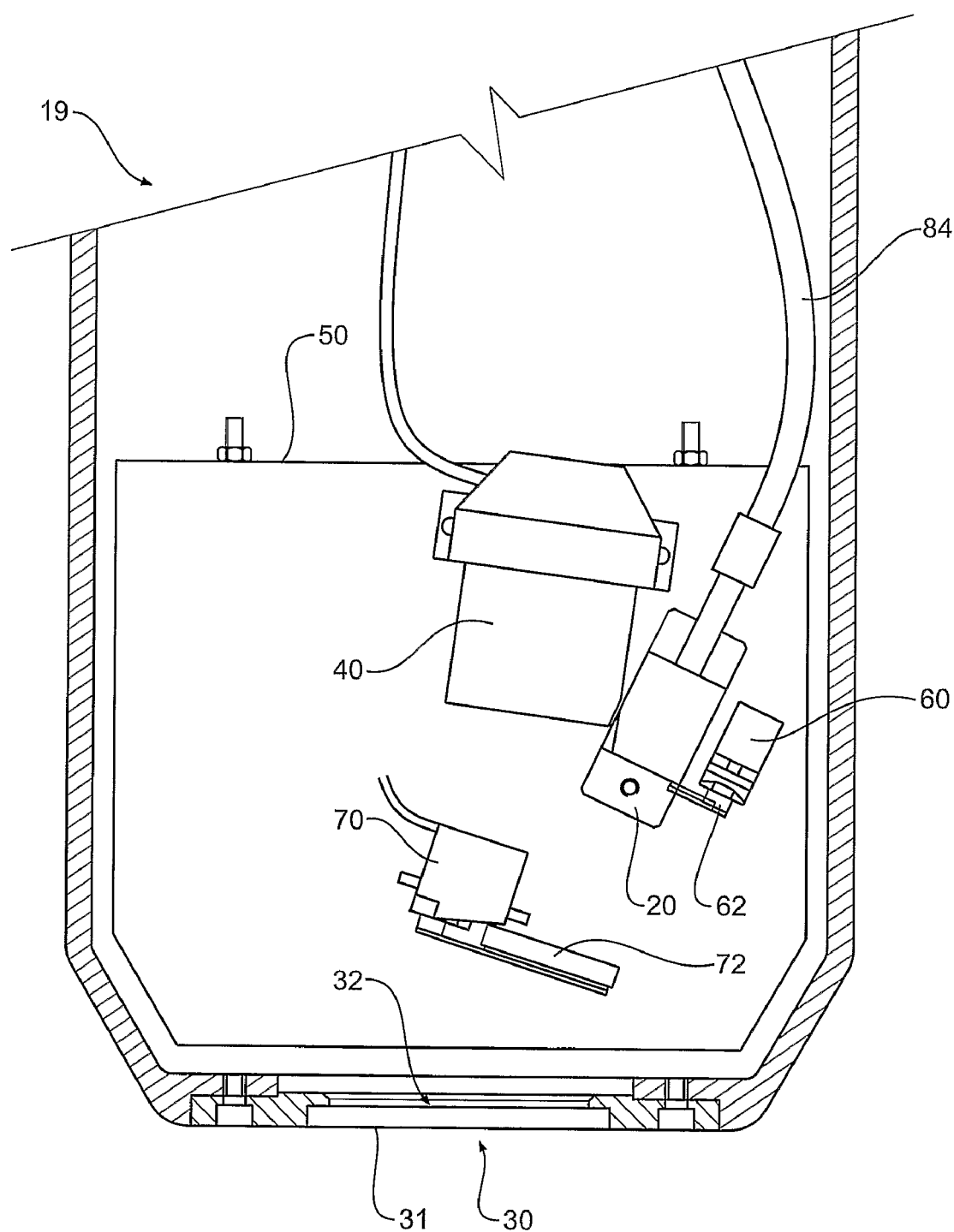
FIG. 5 is a similar view to that of FIG. 3 but shows a further alternative embodiment.

In some applications, it may not be necessary to have the surface 31 of the window 30 angled with respect to the longitudinal axis 50 of the lance. For instance, with some grains, it is not necessary to have the external surface 31 angled as the grain will readily flow across the surface of the window 30 even with the arrangement such as that shown in FIG. 5. Various other heads 19 with windows 30 in various shapes and positions may also be suitable for particular applications.

In other embodiments of the invention, not shown, the external surface 31 of the window 30 may be curved. In some applications, for instance in applications where analysis of bulk quantities of grapes required, it may be important that the (curved) external surface include a sampling area (for instance in the centre of the curved window) angle with respect to a plane normal to a longitudinal axis. This "angling" assists in encouraging bulk product to flow past the sampling area of the external surface as the head is advanced into the bulk product.

The material to be sampled compresses against viewing port 30 during insertion of the lance, ensuring intimate contact and good sample presentation.

Referring again to FIG. 3, the head 19 includes a head portion 19' that is removable from the lance main body 11'. The removable head 19 includes the window 30 which is typically made from fused silica quartz. A seal 17 in the form of an "o" ring is shown in FIG. 3. The major operational components of the spectroscopic lance assembly 10 are advantageously packaged within a sub-assembly 50 as is shown in FIGS. 3 and 4. Sub-assembly 50 is mounted within the cavity 18 so as to avoid transmission of shock and vibration from the lance body 11 to components such as the light source 40 and the spectroscopic receiver 20.

With the embodiments of the invention illustrated in FIGS. 1, 2, 3 and 4, the spectroscopic receiver 20 is connected to a remote spectrometer 29 via optic fibre or fibres 84. In other embodiments of the invention (not shown) the spectrometer 29 may be mounted within the sub assembly 50.

Referring again to FIG. 1, a data processing apparatus 100 is shown. Advantageously, at least part of the data processing is conducted in a data processing apparatus 100 located remote from the spectrometer 29. In some cases, the spectrometer 29 may include at least partial data processing capabilities. Connection between the spectrometer 29 and the data processing apparatus 100 may be wireless.

Figure 6:
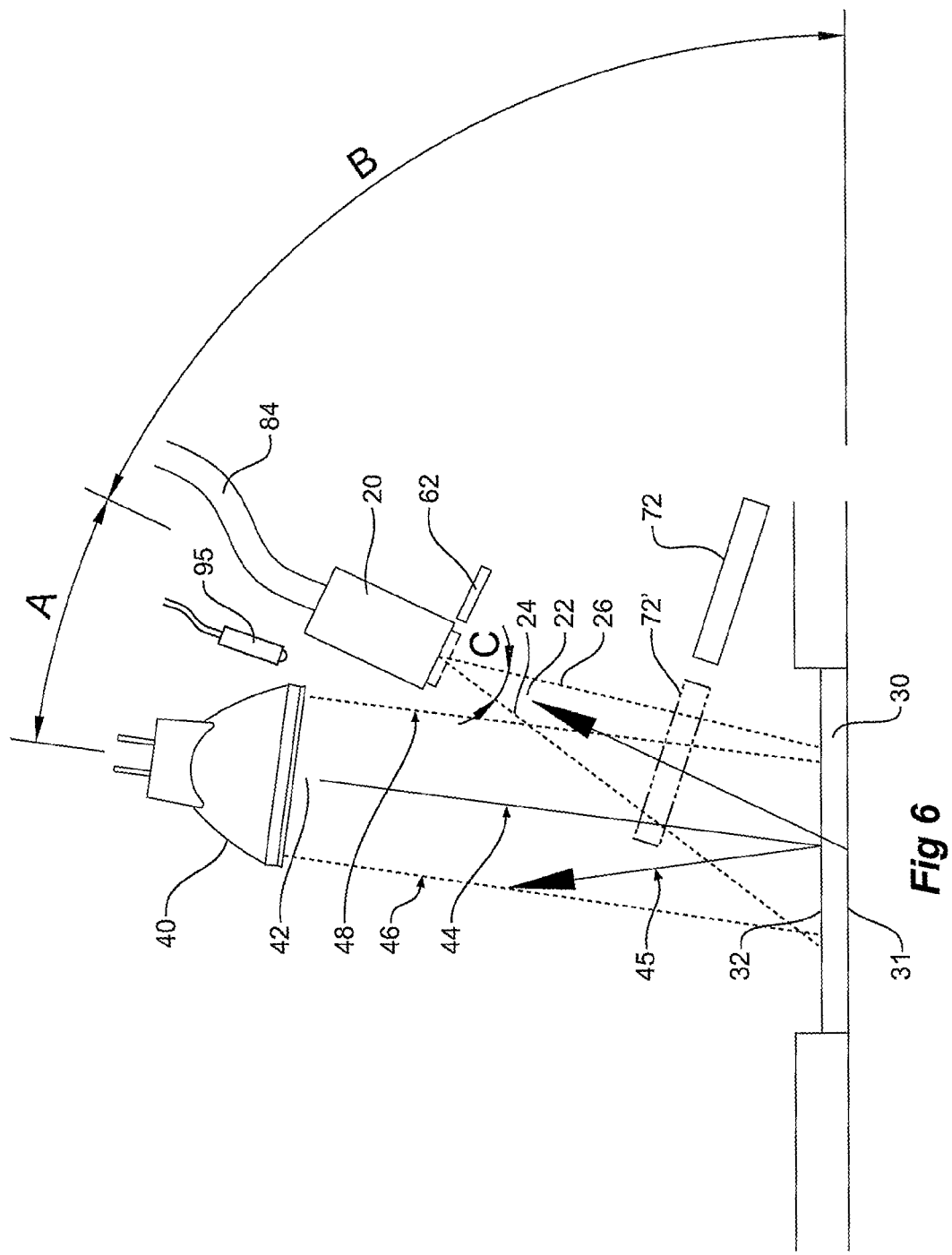
FIG. 6 is a diagrammatic view showing internal components of the lance assembly shown in FIGS. 1 to 4.

Referring to FIG. 6, the light source 40 includes an elliptical reflector which provides a substantially parallel light source with a spectral response matched to the requirements of the spectroscopic receiver 20. The beam of light 42 produced by the light source 40 could be described as a pseudo collimated light source.

Again referring to FIG. 6, it can be seen that both the beam of light 42 and the field of view 22 are orientated at an angle of less than 90° from the planar external surface 31. With this arrangement, direct reflections of the beam of light 42 are directed away from the field of view 22. This is illustrated by arrow 45.

With the embodiment of the invention illustrated in FIG. 6, the field of view is 24°. The bounds of the field of view are indicated by dotted lines 24 and 26.

The lance assembly 10 also includes components allowing internal calibration. Specifically, an actuator 60 moves a cover 62 to block the field of view 22. Furthermore, a standard 72 is movable into the field of view 22 by a further actuator 70. Standard calibration techniques can be used utilising the aforementioned actuators, the cover 62 and the standard 72.

The spectroscopic lance body 11 is typically made from tubular stainless steel of sufficient robustness to allow the lance to be forced into the material 8 being measured.

The control of the direction, speed and penetration motion of the lance is important to provide the descent of the lance through the sample material 8 and the best presentation of the sample at the viewing window or port 30. In some cases, the spectroscopic measurements can be made during penetration; in other cases, the lance may be stationary when the actual readings are taken. In the case of making measurements of the grape juice liquid in the bottom of the truck 9 for determining sugar measurements, in some circumstances the lance can be slowly withdrawn to allow the liquid to displace the solid material.

Referring again to FIG. 1, a driving and positioning mechanism 80, mounted in a framework 90, controls the motion of the lance assembly 10. Complex patterns of insertion and withdrawal to maintain best sample presentation at the window 30 may be achieved. The communication or optical cable bundle 84 moves with the lance to provide transfer of spectral information from the head to the spectrometer 29 and a computer can then interface with other factory systems. In some cases, this cable bundle 84 may be replaced by wireless technology or other forms of data transfer.

The combination of the spectrometer 29 (incorporating its energy source and spectrometer optics) with the spectrometer data processing system 98 allows parameter data for the sample material to be determined by standard spectroscopic methods from spectra detected by the spectrometer and using calibrations derived from chemometric analysis. These parameter data (such as brix, anthocyanins, sucrose etc) are then used by the winemaker to assess the suitability of the grapes for specific wine types and the load of grapes is directed to the appropriate crusher line. Based on these parameter data, the grower is paid according to the weight and "quality" of the grapes ie the value of the grapes to the winery for that season. Other parameters may yield additional data such as information about growing conditions and extraneous matter in the load.

The lance may be fitted with an internal video camera 95 to allow real-time viewing of the sample as presented to the viewing window to ensure correct insertion of the lance. This is shown diagrammatically in FIG. 6. The lance may also be fitted with auxiliary sampling mechanisms to allow physical samples of the test material to be withdrawn for laboratory analysis.

The embodiments of the invention described above allow spectroscopic analysis to be performed during penetration of bulk product. No product needs to be removed for analysis, good statistical data is obtained by scanning a much greater quantity of the product during penetration (and/or removal) of the lance, immediate results are obtained and sampling is many times faster than with previous methods.

One of the attractive features of embodiments of this invention is the ease with which calibration data for the spectroscopic process can be generated. The lance can be immersed in a very small quantity of the test material (just sufficient to cover the viewing port) allowing chemometrics to be performed on limited amounts of material with good statistical outcomes.

Optionally the assembly has a mechanism built into the head of the lance to perform pre-processing of the sample in front of the viewing port for the purpose of allowing better spectroscopic analysis of difficult or very inhomogeneous materials. The pre-processing could consist of an emulsifier, crusher or disintegrator mechanism.

Optionally the apparatus may have other means incorporated into it to remove physical samples for later chemometric determination such as vacuum probes or sampling chambers.

Radiant energy sources or light sources of various types are used in spectroscopy. Depending on the type of spectrometry, radiant energy sources producing energy with wave lengths varying from 150 nanometers to 2500 nanometers may be employed. It should be understood that the term "radiant energy" when used in this specification and its claims includes radiant energy of those wavelengths and hence covers ultra-violet, visible, near infrared and far infrared "light".

The embodiments of the invention described above provide many benefits when parameters which can be derived spectroscopically from samples of bulk material need to be determined in real time. The spectroscopic lance assembly described above is quick and accurate and does not require extraction of sample material from the bulk delivery device. The lance is self cleaning by virtue of its penetrating action. No material is removed or wasted, no chemical process is involved and sampling is far more representative of the whole mass because many contiguous spectral readings can be made as the lance is moving in and out of the material. By making penetrations at a number of points in a load, excellent statistical data are obtained in a very short time, yielding accuracy benefits at sampling points. The methodology is applicable across a wide range of materials from solid to granular to liquids without pre-processing. Reduction in labour requirements at receiving centres, and faster, more accurate business decisions in real time are substantial productivity gains provided by this apparatus.

While the present invention has been described in terms of preferred embodiments in order to facilitate better understanding of the invention, it should be appreciated that various modifications can be made without departing from the principles of the invention. Therefore, the invention should be understood to include all such modifications within this scope.

The claims defining the invention are as follows:

1. A lance assembly for spectroscopically sampling bulk product, the lance assembly comprising:

an elongate lance body having a longitudinal axis, a proximal end for maneuvering and a head at a distal end opposite the proximal end, the head defining a cavity;

a spectroscopic receiver housed within the cavity, the receiver having a field of view and a cover movable to block the field of view of the spectroscopic receiver;

a radiant energy source housed within the cavity providing a beam of energy to be reflected from the bulk product to the receiver; and a window on the head, the window allowing transmission of a reflected spectroscopic signal through the field of view to the receiver from a position adjacent the window, the window having an external surface, in use the external surface in contact with the bulk product;

whereby the beam of energy and the field of view of the receiver are both directed towards the external surface so as to allow sampling adjacent the external surface.

2. The lance assembly as claimed in claim 1 wherein the external surface includes a sampling area angled with respect to a plane normal to the longitudinal axis, whereby in use bulk product flows past the sampling area of the external surface as the head is advanced into the bulk product.

3. The lance assembly as claimed in claim 1 wherein the external surface is planar and wherein the planar external surface is angled with respect to a plane normal to the longitudinal axis, whereby in use bulk product flows past the external surface as the head is advanced into the bulk product.

4. The lance assembly as claimed in claim 3 wherein the planar external surface is angled between 45 and 90 degrees with respect to a plane normal to the longitudinal axis.

5. The lance assembly as claimed in claim 3 wherein both the beam of radiant energy and the field of view of the receiver are orientated at an angle of less than 90 degrees from the planar external surface, whereby direct reflections of the beam of light from surfaces parallel to the external surface are directed away from the field of view.

6. The lance assembly as claimed in claim 1 further comprising a spectrometer housed within the cavity, the spectrometer incorporating the receiver.

7. The lance assembly as claimed in claim 6 wherein the head is removable to facilitate access to the cavity and the spectrometer.

8. The lance assembly as claimed in claim 1 further comprising a camera for imaging analysis, the camera being housed within the cavity.

9. The lance assembly as claimed in claim 8 wherein the camera is positioned angularly between the radiant energy source and the receiver.

10. The lance assembly as claimed in claim 1 further comprising a driving and positioning system for driving and positioning the head into the bulk product.

11. The lance assembly as claimed in claim 10 wherein the driving and positioning system being mounted in a framework, the driving and positioning system and the lance assembly being positionable above a vehicle carrying the bulk product.

12. The lance assembly as claimed in claim 1 further comprising a standard movable to block the field of view of the spectroscopic receiver.

13. The lance assembly as claimed in claim 12 further comprising an actuator for moving the cover, and a further actuator for moving the standard.

14. The lance assembly as claimed in claim 13 wherein the spectroscopic receiver, the radiant energy source, the cover and actuator, and the standard and further actuator are packaged within a sub-assembly, the sub-assembly being mounted within the cavity.

15. A method for spectroscopically sampling bulk product comprising the steps of:

presenting the bulk product in a bulk vessel to an analysis station;

maneuvering an elongate lance assembly having a longitudinal axis, a head at a distal end opposite a proximal end, and a window provided on the head, the head defining a cavity housing a radiant energy source and a spectroscopic receiver with respect to the bulk product so as to penetrate the bulk product within the vessel, whereby a beam of energy and a field of view of the receiver are both directed towards an external surface of the window so as to allow sampling adjacent the external surface and a cover movable to block the field of view of the spectroscopic receiver;

receiving a spectroscopic signal from a sample of the bulk product;

analyzing the spectroscopic signal to provide information as to constituent parameters of the sample; and outputting information pertaining to the constituent parameters of the sample to an operator or to a data collection system.

16. A method for spectroscopically sampling bulk product comprising the steps of:

transporting the bulk product in a vehicle to an analysis station;

maneuvering an elongate lance assembly having a longitudinal axis, a head at a distal end opposite a proximal end, and a window provided on the head, the head defining a cavity housing a radiant energy source and a spectroscopic receiver with respect to the bulk product so as to penetrate the bulk product within the vehicle, whereby a beam of energy and a field of view of the receiver are both directed towards an external surface of the window so as to allow sampling adjacent the external surface and a cover movable to block the field of view of the spectroscopic receiver;

receiving a spectroscopic signal from a sample of the bulk product;

analyzing the spectroscopic signal to provide information as to constituent parameters of the sample; and outputting information on the quality of the sample to an operator.

* * * * *